United States Patent [19]

Baschang et al.

[11] Patent Number: 5,342,977
[45] Date of Patent: Aug. 30, 1994

[54] AMINOSULFONIC ACID DERIVATIVES AND PROCESSES FOR THEIR PREPARATION

[75] Inventors: Gerhard Baschang, Bettingen; Albert Hartmann, Grenzach, both of Switzerland

[73] Assignee: Ciba-Geigy Corp., Ardsley, N.Y.

[21] Appl. No.: 991,938

[22] Filed: Dec. 17, 1992

[30] Foreign Application Priority Data

Dec. 19, 1991 [CH] Switzerland ............... 3776/91

[51] Int. Cl.$^5$ .................................. C07C 233/45
[52] U.S. Cl. ........................... 554/48; 554/85; 554/91; 554/102; 554/42
[58] Field of Search ............ 554/42, 48, 85, 91, 554/102; 574/885, 616

[56] References Cited

U.S. PATENT DOCUMENTS

| | | | |
|---|---|---|---|
| 4,439,425 | 3/1984 | Tarcsay et al. | 424/177 |
| 4,666,886 | 5/1987 | Baschang et al. | 14/17 |

FOREIGN PATENT DOCUMENTS 1139305  1/1983  Canada .

OTHER PUBLICATIONS

Metzger, J. et al. "Synthesis of novel immunologically active tripalmitoyl-S-glycerylcysteinyl lipopetides as useful intermediates for immunogen preparations" Int. J. Peptide Protein Research, 37: 46–57 (1991).

Primary Examiner—José G. Dees
Assistant Examiner—Deborah D. Carr
Attorney, Agent, or Firm—Irving M. Fishman; Karen G. Kaiser

[57] ABSTRACT

Salts of aminosulfonic acid derivatives of formula I

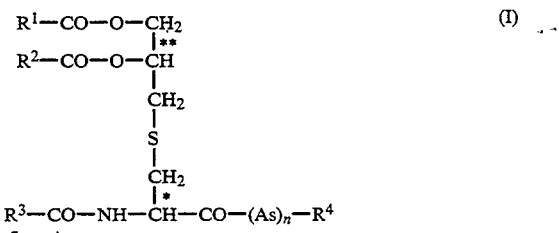

*(R)-configuration
**(R)- or (S)-configuration wherein
$R^1$, $R^2$ and $R^3$ are each independently of the others an aliphatic hydrocarbon radical having from 7 to 21 carbon atoms,
n is 0 or 1,
As is the amidically bonded residue of a (D)- or (L)-amino acid or of a (D)- or (L)-amino acid derivative from the group consisting of Gly, Ala, Ser, Thr, Asp, Asp($R^5$), Glu, Glu($R^5$), Gla, Gla($R^5$) and Gla($R^5$)$_2$, and
$R^4$ and $R^5$ are each independently of the other the amidically bonded radical of an unsubstituted or carboxy-substituted ω-amino-$C_2$–$C_3$alkanesulfonic acid, are described.

Those salts have an immunostimulating action and can be used as medicaments.

10 Claims, No Drawings

AMINOSULFONIC ACID DERIVATIVES AND PROCESSES FOR THEIR PREPARATION

The invention relates to N-acylated derivatives of an unsubstituted or carboxy-substituted ω-amino-$C_2$-$C_3$alkanesulfonic acid, to processes for their preparation, and to their use in the preparation of pharmaceutical compositions and as medicaments, especially as medicaments having an immunostimulating action.

The invention relates especially to salts of aminosulfonic acid derivatives of formula I

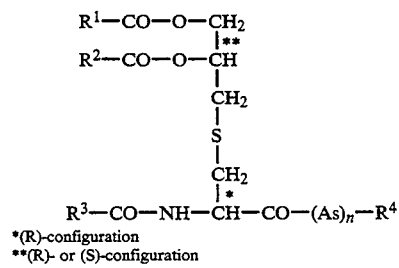

*(R)-configuration
**(R)- or (S)-configuration wherein $R^1$, $R^2$ and $R^3$ are each independently of the others an aliphatic hydrocarbon radical having from 7 to 21 carbon atoms, n is 0 or 1, As is the amidically bonded residue of a (D)- or (L)-amino acid or of a (D)- or (L)-amino acid derivative from the group consisting of Gly, Ala, Ser, Thr, Asp, Asp($R^5$), Glu, Glu($R^5$), Gla, Gla($R^5$) and Gla($R^5$)$_2$, and $R^4$ and $R^5$ are each independently of the other the amidically bonded radical of an unsubstituted or carboxy-substituted ω-amino-$C_2$-$C_3$alkanesulfonic acid.

Salt-forming groups in a compound of formula I are the sulfonic acid groups in the radicals $R^4$ and $R^5$ and free carboxy groups in the radicals As, $R^4$ and $R^5$. Salts of a compound of formula I are metal or ammonium salts and are preferably pharmaceutically acceptable and non-toxic, for example alkali metal or alkaline earth metal salts, for example sodium, potassium, magnesium or calcium salts, or salts with ammonia or suitable organic amines, there being suitable for the salt formation especially aliphatic, cycloaliphatic, cycloaliphatic-aliphatic or araliphatic primary, secondary or tertiary mono-, di- or poly-amines, and also heterocyclic bases, such as lower alkylamines, for example triethylamine, hydroxy-lower alkylamines, for example 2-hydroxyethylamine, bis(2-hydroxyethyl)amine, 2-hydroxyethyldiethyl-amine or tri(2-hydroxyethyl)amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, also bases of the pyridine type, for example pyridine, collidine or quinoline. If several acid groups are present, mono- or poly-salts may be formed.

Pharmaceutically unacceptable salts may also be used for isolation or purification purposes, but only the pharmaceutically acceptable, non-toxic salts are used therapeutically and those are therefore preferred.

An aliphatic hydrocarbon radical $R^1$, $R^2$ or $R^3$ is preferably $C_7$-$C_{21}$alkyl, $C_{17}$alkenyl or $C_{17}$alkynyl. $C_7$-$C_{21}$Alkyl $R^1$, $R^2$ or $R^3$ is preferably straight-chain, for example n-heptyl, n-octyl, n-nonyl, n-decyl, n-undecyl, n-tridecyl, n-pentadecyl, n-hexadecyl, n-heptadecyl, n-nonadecyl or n-heneicosyl. Of the alkyl radicals mentioned, special preference is given to those having from 11 to 17 carbon atoms. $C_{17}$Alkenyl $R^1$, $R^2$ or $R^3$ is preferably (Z)-heptadec-9-en-1-yl, (E)-heptadec-9-en-1-yl, heptadeca-6(Z),9(Z)-dienyl or heptadecatrienyl. $C_{18}$Alkynyl is preferably heptadec-9-yn-1-yl. Thus the acyl radicals $R^1$—CO—, $R^2$—CO— and $R^3$—CO— are preferably derived independently of one another from a $C_8$-$C_{22}$alkanoic acid, a $C_{18}$alkenoic acid or a $C_{18}$alkynoic acid. A $C_8$-$C_{22}$alkanoic acid is especially, for example, caprylic acid (n-octanoic acid), pelargonic acid (n-nonanoic acid), capric acid (n-decanoic acid), undecylic acid (n-undecanoic acid), lauric acid, myristic acid, palmitic acid, margaric acid, stearic acid, arachidic acid (n-eicosanoic acid) or behenic acid (n-docosanoic acid). A $C_{18}$alkenoic acid is especially, for example, oleic acid, elaidic acid, linoleic acid, α-linolenic acid or α- or β-eleostearic acid.

A $C_{18}$alkynoic acid is especially, for example, stearic acid.

$R^1$ and $R^2$ may be different or, preferably, identical.

The abbreviations Gly, Ala, Ser, Thr, Asp, Glu or Gla denote, in that order, the amino acids glycine, alanine, serine, threonine, aspartic acid, glutamic acid and γ-carboxyglutamic acid, respectively.

In accordance with the internationally recognised rules of nomenclature, in this Application the abbreviations for the amino acids denote the free acid and, unless otherwise indicated, the L-configuration. The α-amino group is to be regarded as being to the left of the abbreviation and the carboxy group to the right. The absence of a H atom in the α-amino group is shown by a bond to the left of the abbreviation for the amino acid and the absence of two H atoms is shown by two bonds to the left. The absence of a HO group in the carboxy group is expressed by a bond to the right. Substituents in the side chain of amino acids are placed in brackets immediately after the amino acid symbol. Thus, for example, palmitoyl-Cys[2(R,S),3-dilauroyloxy-propyl] represents N-palmitoyl-S-[2(R,S),3-dilauroyloxy-propyl]-(R)-cysteine.

An ω-amino-$C_2$-$C_3$alkanesulfonic acid is, for example, homotaurine of the formula $H_2N$—$(CH_2)_3$—$SO_3H$ or preferably taurine of formula $H_2N$—$(CH_2)_2$—$SO_3H$. A carboxy-substituted ω-amino-$C_2$-$C_3$alkanesulfonic acid is preferably a cysteine acid of the formula $H_2N$-$CH(COOH)$-$CH_2$-$SO_3H$, especially in the (L)-configuration.

The salts of the sulfonic acid derivatives of formula I have valuable pharmacological, especially immunostimulating, properties.

For example, at a dose as low as 0.02 nanogram/0.2 ml of culture medium, those salts are capable of activating tumoricidal rat alveolar macrophages in vitro, with the result that after incubation with the salt the macrophages are capable of destroying tumour cells.

Those salts also induce in vitro the release of interleukin-1β and tumour necrosis factor (TNFα) from human monocytes.

The novel compounds are also distinguished in in vivo models by a high degree of biological activity: NMRI mice are immunised by intraperitoneal injection of 10 μg of bovine serum albumin (BSA) on day 0. 8, 18 and 28 days later, serum samples are taken and examined for their anti-BSA antibody content using a passive haemagglutination technique. At the dose used, the BSA is subimmunogenic to the receiver animals, that is to say, it is not capable of triggering any antibody production or is capable of triggering only a negligible amount of antibody production. In this test, when administered intraperitoneally on the day of immunisation, the salts of the compounds of formula I are able to bring about a significant increase in the production of antibodies to BSA. Special mention should be made of the good activity of the novel compounds when administered subcutaneously.

In contrast to C57BL/6 mice, MAGf mice are susceptible to infection by L. monocytogenes. 72 and 24 hours before being infected, MAGf mice are treated perorally with a suspension of 1 mg/kg of a compound of formula I in squalene or with an equivalent volume of squalene. The mice are then infected intravenously with $1 \times 10^4$ CFU (colony forming units) of L. monocytogenes EX 1. 10 days after infection the survival rate in the group of MAGf mice treated with a compound of formula I is found to be significantly higher, for example 80%, than in the group of mice treated with an equivalent volume of squalene (20%). The survival rate of C57BL/6 mice treated with squalene is 90%.

12–15-month old C57BL/6 mice are susceptible to infection with H. influenzae, while younger, 6–8-week old mice are resistant. 72 and 24 hours before being infected, the mice are treated perorally with a suspension of 1 mg/kg of a compound of formula I in squalene or with an equivalent volume of squalene. The mice are then infected intravenously with $1 \times 10^5$ CFU (colony forming units) of H. influenzae P27. 10 days after infection, the survival rate in the group of older mice treated with a compound of formula I is found to be significantly higher, for example 70%, than in the group of mice treated with an equivalent volume of squalene (10%). Of the younger mice treated with squalene, 80% survive.

As adjuvants in admixture with vaccines or chemically bonded to vaccines, for example suitable antigens or haptens, the novel salts of the compounds of formula I can be used to increase the success of vaccinations and to enhance the resistance to infection by bacterial, viral or parasitic pathogens that is imparted by humoral antibodies and/or by cellular immunity.

The novel salts can be used to promote immune responses in humans and animals. The salts are therefore suitable especially for stimulating the body's own resistance, for example in the case of cancer, chronic and acute infections or selective (antigen-specific) immunodeficiency, as well as in the case of both congenital, and acquired, general (i.e. non-antigen-specific) immunological defective states, such as those that occur with age, in the course of serious primary diseases and especially after therapy with ionising rays or with immunosuppressive medicaments. The compounds mentioned can also be administered in combination with antibiotics, chemotherapeutic agents or other substances in order to counteract immunological damage. Finally, the compounds described are also suitable for the general prophylaxis of infectious diseases in humans and animals.

The dose of active ingredient depends inter alia on the species of warm-blooded animal, the defensive condition of the organism, the method of administration and the nature of the disease. The dose-effect relationship is relatively slight.

The therapeutic dose for warm-blooded animals having a body weight of approximately 70 kg, for example for humans, is from 0.1 mg to 25 mg per day, preferably from 0.2 to 10 mg, generally from 0.5 mg to 5 mg, for example 2 mg, for example in the case of intravenous administration. The dose in the case of topical application is lower by a factor of up to 10.

Preference is given to the salts of sulfonic acid derivatives of formula I wherein $R^1$, $R^2$ and $R^3$ are each independently of the other $C_7$–$C_{21}$alkyl, $C_{17}$alkenyl or $C_{17}$alkynyl, n is 0 or 1, As is the amidically bonded residue of an amino acid or of an amino acid derivative from the group consisting of Ala and Glu($R^5$), and $R^4$ and $R^5$ are each the amidically bonded radical of an $\omega$-amino-$C_2$–$C_3$alkanesulfonic acid.

Special preference is given to the salts of sulfonic acid derivatives of formula I wherein $R^1$ and $R^2$ are identical and are each straight-chain $C_{11}$–$C_{17}$alkyl, $R^3$ is straight-chain $C_{11}$–$C_{17}$alkyl, n is 0 or 1, As is the amidically bonded residue of alanine or Glu(NH—CH$_2$—CH$_2$—SO$_3$H), and $R^4$ is the amidically bonded radical of 2-aminoethanesulfonic acid.

Very special preference is given to the above-mentioned salts wherein formula I $R^1$ is n-undecyl, $R^2$ is n-undecyl and $R^3$ is n-pentadecyl.

The greatest preference is given to the salts of the compounds of formula I that are described in the Examples.

The salts of the compounds of formula I are prepared in a manner known per se.

they are prepared, for example, as follows:

a) a compound of formula II

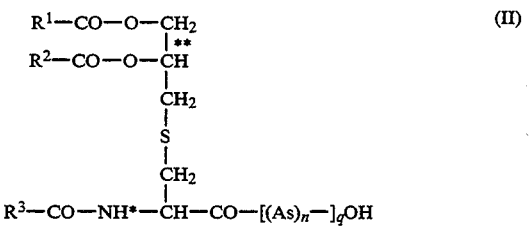

*(R)—configuration
**(R)— or (S)—configuration wherein q is 0 or 1 and $R^1$, $R^2$, $R^3$, n and As are as defined above, free functional groups present in the As residue, with the exception of the group that is to participate in the reaction, being protected if necessary by readily removable protecting groups, or a reactive carboxylic acid derivative thereof, is reacted with a salt of a compound of formula III

wherein r is 1 if in the co-reactant of formula II q is 0, or r is 0 if q is 1, and wherein As, n and $R^4$ are as defined above, free functional groups present in the radicals As and $R^4$, with the exception of the group that is to participate in the reaction, being protected if necessary by readily removable protecting groups, and any protecting groups present are removed, or b) a salt of a compound of formula IV

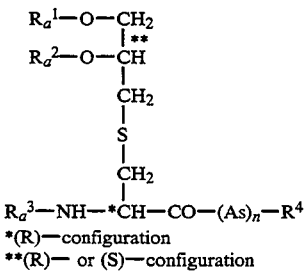

(IV)

*(R)—configuration
**(R)— or (S)—configuration wherein $R^1{}_a$ is hydrogen or the above-mentioned radical $R^1$—CO—, $R^2{}_a$ is hydrogen or the above-mentioned radical $R^2$—CO— and $R^3{}_a$ is hydrogen or the above-mentioned radical $R^3$—CO—, with the proviso that at least one of the radicals $R^1{}_a$, $R^2{}_a$ and $R^3{}_a$ must be hydrogen, and wherein As, n and $R^4$ are as defined above, free functional groups present in the radicals As and $R^4$, with the exception of the group that is to participate in the reaction, being protected if necessary by readily removable protecting groups, is reacted with a carboxylic acid of formula V $$R^6\text{—COOH} \qquad (V),$$

wherein $R^6$ is an aliphatic hydrocarbon radical having from 7 to 21 carbon atoms, or with a reactive carboxylic acid derivative thereof, and any protecting groups present are removed, or c) a compound of formula VI

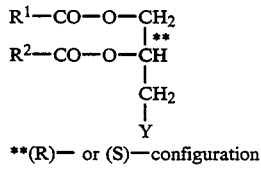

(VI)

**(R)— or (S)—configuration wherein Y is a nucleofugal group and $R^1$ and $R^2$ are as defined above, is reacted with a salt of a compound of formula VII

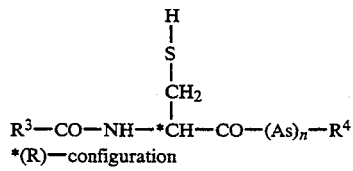

(VII)

*(R)—configuration wherein the substituents are as defined above, free functional groups, with the exception of the mercapto group that participates in the reaction, being protected if necessary by readily removable protecting groups, or with a reactive derivative of a compound of formula VII, and any protecting groups present are removed, or d) a compound of formula VIII

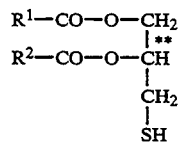

(VIII)

**(R)— or (S)—configuration wherein $R^1$ and $R^2$ are as defined above, or a reactive derivative of that compound, is reacted with a salt of a compound of formula IX

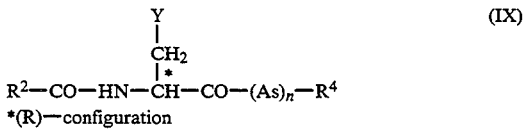

(IX)

*(R)—configuration wherein Y is a nucleofugal group and the remaining substituents are as defined above, free functional groups being if necessary in protected form, and any protecting groups present are removed, and, if desired, after carrying out one of process variants a–d), a resulting salt is converted into a different salt and, if desired, a resulting mixture of isomers is separated.

The procedure for carrying out the above-mentioned process variants is explained in detail below:

Preference is given to processes b) and, especially, a).

Process a

Free functional groups that may be present in compounds of formulae II and III and that are protected by readily removable protecting groups are especially free carboxy groups that are not to be acylated. The protection of free hydroxy in the As radical is optional, i.e. not absolutely essential.

Protecting groups, their introduction and removal are described, for example, in "Protective Groups in Organic Chemistry", Plenum Press, London, N.Y. 1973, and in "Methoden der organischen Chemie", Houben-Weyl, 4th edition, Vol. 15/1, GeorgThieme-Verlag, Stuttgart 1974, and in Theodora W. Greene, "Protective Groups in Organic Synthesis", John Wiley & Sons, New York 1981. A characteristic of protecting groups is that they can be removed readily, i.e. without undesired secondary reactions taking place, for example by solvolysis, reduction, photolysis or under physiological conditions.

Hydroxy-protecting groups are, for example, acyl radicals, such as unsubstituted or substituted, for example halo-substituted, lower alkanoyl, such as 2,2-dichloroacetyl, or acyl radicals of carbonic acid semi-esters, especially tert-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, also trityl or formyl, or organic silyl or stannyl radicals, and also readily removable etherifying groups, such as tert-lower alkyl, for example tert-butyl, 2-oxa- or 2-thia-aliphatic or 2-oxa- or 2-thia-cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogs, and unsubstituted or substituted 1-phenyl-lower alkyl, such as unsubstituted or substituted benzyl or diphenylmethyl, examples of suitable substituents of the phenyl radicals being halogen, such as chlorine, lower alkoxy, such as methoxy, and/or nitro. Carboxy groups are customarily protected in esterified form, such ester groupings being readily removable under mild conditions. A carboxy group protected in that manner contains as esterifying group especially a lower alkyl group that is branched in the 1-position or substituted in the 1- or 2-position by suitable substituents. Preferred carboxy groups present in esterified form are inter alia tert-lower alkoxycarbonyl, for example tert-butoxycarbonyl, arylmethoxycarbonyl having one or two aryl radicals, wherein aryl is a phenyl radical that is unsubstituted or mono- or poly-substituted, for example, by lower alkyl, such as tert-lower alkyl, for example tert-butyl, lower alkoxy, such as methoxy, hydroxy, halogen, for example chlorine, and/or by nitro, such as benzyloxcarbonyl that is unsubstituted or substituted, for example, as mentioned above, for example 4-methoxybenzyloxycarbonyl or 4-nitrobenzyloxycarbonyl, or diphenylmethoxycarbonyl that is unsubstituted or substituted, for example, as mentioned above, for example diphenylmethoxycarbonyl or di(4-methoxyphenyl)methoxycarbonyl, 1-lower alkoxy-lower alkoxycarbonyl, for example methoxymethoxycarbonyl, 1-methoxyethoxycarbonyl or 1-ethoxymethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, such as corresponding, unsubstituted or substituted lower alkyl, phenyl-lower alkyl, cycloalkyl or phenyl, for example 2-tri-lower alkylsilylethoxycarbonyl, 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

The organic silyl or stannyl radicals mentioned hereinbefore and hereinafter preferably contain lower alkyl, especially methyl, as substituents of the silicon or tin atoms. Corresponding silyl or stannyl groups are especially tri-lower alkylsilyl, more especially trimethylsilyl, also dimethyl-tert-butyl-silyl, or correspondingly substituted stannyl, for example tri-n-butylstannyl.

Preferred protected carboxy groups are tert-lower alkoxycarbonyl, such as tert-butoxycarbonyl, and especially benzyloxycarbonyl that is unsubstituted or substituted, for example, as mentioned above, such as 4-nitrobenzyloxycarbonyl, or diphenylmethoxycarbonyl, especially 2-(trimethylsilyl)-ethoxycarbonyl.

Reactive carboxylic acid derivatives of a compound of formula II that can be used as acylating agents for acylating a compound of formula III are especially reactive activated esters or reactive anhydrides, also reactive cyclic amides, it being possible for the activation of the carboxylic acid used as acylating agent also to take place in situ in the presence of the compound of formula III.

Activated esters of acids are especially esters unsaturated at the linking carbon atom of the esterifying radical, for example of the vinyl ester type, such as vinyl esters themselves (obtainable, for example, by transesterification of a corresponding ester with vinyl acetate; activated vinyl ester method), carbamoyl vinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide or 1-hydroxybenzotriazole, for example by the anhydride or carbodiimide method; activated N-hydroxy esters method) or silyl esters (that are obtainable, for example, by treatment of the corresponding acid with a silylating agent, for example hexamethyldisilazane, and that react readily with hydroxy groups but not with amino groups).

Anhydrides of acids may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide by treatment thereof with nitrous acid; azide method), anhydrides with carbonic acid semi-derivatives, such as corresponding esters, for example carbonic acid lower alkyl semi-esters. (obtainable, for example, by treatment of the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), or anhydrides with organic acids, such as mixed anhydrides with organic carboxylic acids (obtainable, for example, by treatment of the corresponding acid with an unsubstituted or substituted lower alkane- or phenylalkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid, with a suitable organic sulfonic acid halide, such as lower alkane- or aryl-, for example methane- or p-toluene-sulfonic acid chloride, mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (obtainable, for example, by treatment of the corresponding acid with N,N'-carbonyldiimidazole; imidazolide method), or pyrazoles, for example 3,5-dimethylpyrazole (obtainable, for example, via the acid hydrazide by treatment with acetylacetone; pyrazolide method).

As mentioned, derivatives of acids that are used as acylating agents can also be formed in situ. For example, N,N'-disubstituted amidino esters can be formed in situ by reacting a mixture of the starting material of formula III and the acid used as acylating agent, in the presence of a suitable N,N-disubstituted carbodiimide, for example N,N'-dicyclohexylcarbodiimide. In addition, amino or amido esters of the acids used as acylating agents can be formed in the presence of the starting material of formula III to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, N-hydroxynorbornane-2,3-dicarboximide or N-hydroxybenzotriazole, where appropriate in the presence of a suitable base, for example 4-dimethylaminopyridine or tetramethylguanidine.

The compounds of formula III are preferably used in the form of their alkali metal salts, such as, especially, their sodium salts.

The reaction can be carried out in a manner known per se, the reaction conditions depending especially on whether and how the carboxy group of the acylating agent has been activated, customarily in the presence of a suitable solvent or diluent or of a mixture thereof, and, if necessary, in the presence of a condensation agent which, for example if the carboxy group participating in the reaction is in the form of an anhydride, may also be an acid-binding agent, with cooling or heating, for example in a temperature range of from approximately $-30°$ C. to approximately $+150°$ C., especially from approximately $0°$ C. to $+70°$ C., preferably from room temperature (approximately $+20°$ C.) to $+40°$ C., in a closed reaction vessel and/or under the atmosphere of an inert gas, for example nitrogen. Examples of customary condensation agents are carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example 2-ethoxy-1-ethoxycarbonyl-1,2-dihydroquinoline. Examples of customary acid-binding condensation agents are alkali metal carbonates or hydrogen carbonates, for example sodium or potassium carbonate or hydrogen carbonate (customarily together with a sulfate), or organic bases, such as customarily sterically hindered tri-lower alkylamines, for example N,N-diisopropyl-N-ethylamine.

The removal of protecting groups that are not constituents of the desired end product of formula I, for example the carboxy-, amino-, hydroxy- or carbamoyl-protecting groups, is effected in a manner known per se, for example by means of solvolysis, especially hydrolysis, alcoholysis or acidolysis, or by means of reduction, especially hydrogenolysis or chemical reduction, optionally stepwise or simultaneously, it being possible also to use enzymatic methods.

For example, tert-lower alkoxycarbonyl, or lower alkoxycarbonyl substituted in the 2-position by an organic silyl group or in the 1-position by lower alkoxy or lower alkylthio, or unsubstituted or substituted diphenylmethoxycarbonyl can be converted into free carboxy, for example, by treatment with a suitable acid, such as formic acid or trifluoroacetic acid, optionally with the addition of a nucleophilic compound, such as phenol or anisole. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can also converted into free carboxy by chemical reduction, for example by treatment with an alkali metal dithionite, for example sodium dithionite, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenyl-glycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can also be cleaved by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid that yields the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylaryl-ammonium fluoride, for example tetraethylammonium fluoride or tetrabutylammonium fluoride, in the presence of an aprotic polar solvent, such as dimethyl sulfoxide or N,N-dimethylacetamide.

Hydroxy protected by unsubstituted or substituted 1-phenyl-lower alkyl, for example benzyl, is preferably freed by catalytic hydrogenation, for example in the presence of a palladium-on-carbon catalyst. A hydroxy group protected by 2,2-dichloroacetyl is freed, for example, by basic hydrolysis, and a hydroxy group etherified by tert-lower alkyl or by a 2-oxa- or 2-thia-aliphatic or 2-oxa- or 2-thia-cycloaliphatic hydrocarbon radical is freed by acidolysis, for example by treatment with a mineral acid or a strong carboxylic acid, for example trifluoroacetic acid.

Hydroxy etherified by an organic silyl radical, for example trimethylsilyl, can also be freed using a salt of hydrofluoric acid that yields fluoride anions, for example tetrabutylammonium fluoride.

When several protected functional groups are present, the protecting groups are preferably so selected that more than one such group can be removed at the same time, for example by acidolysis, such as by treatment with trifluoroacetic acid or formic acid, or by reduction, such as by treatment with zinc and acetic acid, or with hydrogen and a hydrogenation catalyst, such as a palladium/carbon catalyst.

The preparation of the starting materials of formula II is described in the European Patent Applications having publication numbers 330 and 114 787.

Process b

The compounds of formula IV are preferably used in the form of their alkali metal salts, for example their sodium salts.

In a compound of formula IV, free functional groups that may be present in the radicals As and $R^4$ and that have to be protected by a readily removable protecting group are especially free hydroxy groups, but also free carboxy groups. Suitable protecting groups and their removal are described above in Process a).

A reactive carboxylic acid derivative of a compound of formula V is especially a reactive ester, a reactive anhydride or a reactive cyclic amide, wherein the carboxy group has been activated analogously to the reactive acylating agents described in Process a), it being possible for the activation also to be carried out in situ.

If necessary, the esterification can be carried out in the presence of suitable condensation agents: when using free carboxylic acids of formula V, for example, it can be carried out in the presence of carbodiimide compounds, such as dicyclohexylcarbodiimide, or carbonyl compounds, such as diimidazolylcarbonyl, and when using reactive acid derivatives, for example, in the presence of basic agents, such as tri-lower alkylamines, for example triethylamine, or heterocyclic bases, for example pyridine or 4-dimethylaminopyridine. The acylating reaction can be carried out in the absence or, preferably, in the presence of a solvent or solvent mixture, with cooling, at room temperature or preferably with heating, especially at from 20° C. to 120° C. and, if necessary, in a closed vessel and/or under an inert gas atmosphere, for example a nitrogen atmosphere. Examples of suitable solvents are unsubstituted or substituted, especially chlorinated, aliphatic, cycloaliphatic or aromatic hydrocarbons, such as carbon tetrachloride/pyridine (1:1), benzene or toluene.

A preferred form of Process b) is the esterification of a compound of formula IV wherein $R^1_a$ and $R^2_a$ are each hydrogen and $R^3_a$ is the above-mentioned radical $R^3$-CO-.

The starting materials of formula IV are obtained in a manner analogous to that described in the European Patent Applications having publication numbers 330 and 114 787. For example, $R^3$-CO-Cys is obtained from (R)-cysteine by acylation with $R^3$-CO-Cl in pyridine/methylene chloride and converted with glycerol glycide into $R^3$-CO-Cys-[2(R,S),3-dihydroxy-propyl], from which $R^3$-CO-Cys[2(R,S),3-dihydroxy-propyl]-$(As)_n$-$R^4$ is obtained by reaction with a compound of formula III analogously to Process a).

Process c

A nucleofugal group Y is a leaving group in a nucleophilic substitution reaction, preferably reactive esterified hydroxy, for example hydroxy esterified by a strong inorganic or organic acid, such as hydroxy esterified by a mineral acid, for example a hydrohalic acid, such as hydrochloric acid, hydrobromic acid or hydriodic acid, also sulfuric acid, or halosulfuric acid, for example fluorosulfuric acid, or by a strong organic sulfonic acid, such as a lower alkanesulfonic acid that is unsubstituted or substituted, for example by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic acid, trifluoromethanesulfonic acid or p-toluenesulfonic acid, and is preferably a chloride, bromide or iodide.

The salt of a compound of formula VII used is preferably an alkali metal salt, for example a sodium salt.

Functional groups in a compound of formula VII that are preferably protected by readily removable protecting groups are hydroxy and carboxy. Suitable protecting groups and their removal are described above in Process a).

A reactive derivative of a compound of formula VII is a compound in which the nucleophilicity of the sulfur atom participating in the reaction has been enhanced, for example by removal of the proton of the mercapto group. Such a reactive derivative can, if desired, also be formed in situ.

The reaction can be carried out, for example, in a manner analogous to that described in the European Patent Applications having publication numbers 330 and 114 787. The reaction is preferably carried out at approximately from −20° C. to +120° C., especially from 0° C. to +40° C., for example at 0° C., for example in absolute dimethylformamide in the presence of diazabicycloundecene and under protective gas.

The starting materials of formula VI are known. The starting materials of formula VII are obtained, for example, by reacting $R^3$-CO-Cys, the mercapto group of which is preferably protected by a readily removable protecting group, with H-$(As)_n$-$R^4$ in accordance with Process a) and removal of the protecting group(s).

Process d

A reactive derivative of a compound of formula VIII is a compound in which the nucleophilicity of the sulfur atom participating in the reaction has been enhanced, for example by removal of the proton of the mercapto group. Such a reactive derivative can, if desired, also be formed in situ.

A nucleofugal group Y is, for example, one of the groups mentioned in Process c).

Functional groups in a compound of formula IX that are preferably in protected form are hydroxy and carboxy groups. Suitable protecting groups and their removal are described above in Process a).

Unless otherwise indicated hereinbefore, Processes a) to f) are carried out in an inert solvent or solvent mixture at a temperature of from approximately −20° C. to approximately +120° C., and, if necessary, under protective gas.

The starting materials for the processes according to the present invention described above are known, for example from the European Patent Applications having publication numbers 330 or 114 787, or they can be prepared in a manner known per se, for example analogously to the above-mentioned processes.

Additional operations: Salts of compounds of formula I can be prepared in a manner known per se. For example, salts of compounds of formula I can be formed by reaction with a suitable base, for example by treatment with suitable metal compounds, such as alkali metal salts of suitable organic carboxylic acids, for example the sodium salt of α-ethylcaproic acid, or with suitable inorganic alkali metal or alkaline earth metal salts, especially those that are derived from a weak and preferably volatile acid, for example sodium hydrogen carbonate, or with ammonia or a suitable organic amine. For the formation of alkali metal salts from salts of the compounds of formula I having divalent or trivalent ions, for example calcium ions, it is possible, advantageously, to react the last-mentioned salts with an alkali metal salt of a complex former that has a greater binding affinity with the divalent or trivalent ions than with the monovalent alkali metal ions, for example with the sodium salt of ethylenediaminetetraacetic acid.

In view of the close relationship between the salts of the compounds of formula I and the free acids, within the context of this text, the term "salts" should be understood, where appropriate and expedient, as meaning also salt/acid mixtures having a certain percentage of free acid, especially when the medium has a suitably low pH value.

Mixtures of isomers can be separated into the individual isomers in a manner known per se, for example by fractional crystallisation, chromatography, etc.

Unless otherwise indicated, the processes described above, including the processes for the removal of protecting groups and the additional process steps, are carried out in a manner known per se, for example in the presence or absence of solvents or diluents, if necessary in the presence of condensation agents or catalysts, at reduced or elevated temperature, for example in a temperature range of from approximately −20° C. to approximately +150° C., especially from approximately +1° C. to approximately +70° C., more especially from room temperature (approximately +20° C.) to +45° C., in a suitable vessel and if necessary under pressure, for example the inherent pressure of the system, or under an inert gas atmosphere, for example a nitrogen atmosphere.

If necessary, taking into consideration all the substituents present in the molecule, for example when readily hydrolysable radicals are present, especially mild reaction conditions should be used, such as short reaction times, the use of mild acidic or basic agents in low concentrations, stoichiometric quantity ratios and the selection of suitable catalysts, solvents, temperature and/or pressure conditions.

The invention relates also to those forms of the process according to which a compound obtainable as intermediate at any stage of the process is used as starting material and the remaining process steps are carried out or the process is interrupted at any stage or a starting material is formed under the reaction conditions or is used in the form of a reactive derivative or a salt. The starting materials used are preferably those that in accordance with the process result in the compounds described above as being especially valuable.

The present invention relates also to novel starting materials and/or intermediates and to processes for their preparation. The starting materials used and the reaction conditions chosen are preferably those which result in the compounds described in this Application as being especially preferred.

The invention relates also to pharmaceutical compositions comprising an effective amount, especially an immunostimulating amount, of the active ingredient together with pharmaceutically acceptable carriers, that are suitable for topical, including, for example, intranasal, or parenteral, for example intravenous, subcutaneous or intraperitoneal, or enteral, e.g. oral, administration.

Suitable for parenteral administration are especially aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran, and, optionally, also stabilisers.

The pharmaceutical compositions for parenteral administration in ready-for-use form comprise preferably from 0.1% to 20%, especially from 1% to 10%, active ingredient. Dry-filled ampoules that are not "ready-for-use" may contain up to 100% active ingredient.

Examples of compositions that may be used for topical administration are creams, ointments, pastes, foams, tinctures and solutions comprising preferably from approximately 0.02% to approximately 2% active ingredient.

Creams are oil-in-water emulsions that comprise more than 50% water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens), and also polyoxyethylene fatty alcohol ethers or fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl alcohol or stearyl alcohol. Additives to the aqueous phase are, inter alia, agents that reduce the drying-out of the creams, for example polyalcohols, such as glycerol, sorbitol, propylene glycol and/or polyethylene glycols, and also preservatives and perfumes.

Ointments are water-in-oil emulsions that comprise up to 70%, but preferably from approximately 20% to approximately 50%, water or aqueous phase. Suitable as fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerol, propylene glycol, sorbitol and/or polyethylene glycol, and also preservatives and perfumes.

Fatty ointments are anhydrous and contain as base especially hydrocarbons, for example paraffin, petroleum jelly and/or liquid paraffins, also natural or partially synthetic fats, for example coconut fatty acid triglyceride, or preferably hardened oils, for example hydrogenated groundnut oil or castor oil, also fatty acid partial esters of glycerol, for example glycerol mono- and di-stearate, and also, for example, the fatty alcohols increasing the water-absorption capacity, emulsifiers and/or additives mentioned in connection with the ointments.

Pastes are creams and ointments having secretion-absorbing powder constituents, such as metal oxides, for example titanium oxide or zinc oxide, also talcum and/or aluminium silicates, the purpose of which is to bind any moisture or secretions present.

Foams are administered from pressurised containers and are liquid oil-in-water emulsions in aerosol form; halogenated hydrocarbons, such as chlorofluoro-lower alkanes, for example dichlorodifluoromethane and dichlorotetrafluoroethane, are used as propellants. As oil phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of emulsifiers having predominantly hydrophilic properties, such as polyoxyethylene sorbitan fatty acid esters (Tweens), and emulsifiers having predominantly lipophilic properties, such as sorbitan fatty acid esters (Spans). The customary additives, such as preservatives, are also added.

Tinctures and solutions generally have an aqueous-ethanolic base to which there are added, inter alia, polyalcohols, for example glycerol, glycols, and/or polyethylene glycol, as humectants for reducing evaporation, and fat-restoring substances, such as fatty acid esters with low molecular weight polyethylene glycols, that is to say lipophilic substances that are soluble in the aqueous mixture, as a replacement for the fatty substances removed from the skin by the ethanol, and, if necessary, other adjuncts and additives.

The manufacture of the topically administrable pharmaceutical compositions is effected in a manner known per se, for example by dissolving or suspending the active ingredient in the base or, if necessary, in a portion thereof. When the active ingredient is formulated as a solution, it is generally dissolved in one of the two phases before emulsification; when the active ingredient is formulated as a suspension, it is mixed with a portion of the base after emulsification and then added to the remainder of the formulation.

Especially advantageous is the use of pharmaceutical compositions in liposome form. The lipopeptide is added during the formation of the liposomes. The preparation of the liposomes and the incorporation of the active ingredient can be effected in various ways and are described in the review by Kaye, St. B., Cancer Treatment Reviews (1981) 8, 27–50. Other processes for the preparation of liposomes as carriers for active ingredients are likewise described by Barenholz et al. in Biochemistry, Vol. 16, No. 12, 2806–2810, and in German Offenlegungsschriften (DOS) 28 19 655, 29 02 672, 25 32 317 and 28 42 608, in U.S. Pat. No. 4,053,585 and in European Patent Application 36 676.

For example, the lipid components, for example phospholipids, for example phosphatidic acid, lecithin or cephalin, and if appropriate neutral lipids, for example cholesterol, are dissolved together with the lipopeptide in an organic solvent, for example chloroform/methanol. After concentration by evaporation, a homogeneous film layer remains. The film layer is dispersed in an aqueous phase, for example by shaking, yielding multi-lamellar liposomes. In the subsequent treatment with ultrasound, depending on the duration of the exposure to ultrasonic waves, unilamellar liposomes containing the active ingredient may be formed. The liposome suspensions can be used especially for parenteral, for example subcutaneous or intraperitoneal, administration, as well as topical, for example intranasal, application.

The present invention includes especially also the use of the novel lipopeptides of formula (I) and of their mentioned derivatives in a method of stimulating the immune system, the novel compounds preferably being administered in the form of the pharmaceutical compositions described above.

The Examples that follow illustrate the invention described above, but do not limit the invention in any way. Temperatures are given in degrees Celsius. $R_F$ values are determined on silica gel thin-layer plates (Merck, Darmstadt, Germany). Unless otherwise indicated, the composition of solvent mixtures is given in parts by volume. In the case of optical rotation, the concentration, c, of the substance in the solvent (mixture) is given as a percentage (weight/volume).

EXAMPLE 1

0.344 g (2.75 mmol) of 2-aminoethanesulfonic acid (taurine) and 0.5 g (2.76 mmol) of N-hydroxynorbornane-2,3-dicarboximide are suspended in 5 ml of twice-distilled water and, with stirring, the pH is adjusted to 7 with 0.1N sodium hydroxide solution. The solution is concentrated by evaporation in vacuo to form a resin which is dissolved in a mixture of 12 ml of dimethylacetamide and 3 ml of water. A solution of 2 g (2.5 mmol) of N-palmitoyl-S-[2(R),3-dilauroyloxy-propyl]-(R)-cysteine in 5 ml of dimethylacetamide and 0.7 g of N,N'-dicyclohexylcarbodiimide is then added. The mixture is stirred for 18 hours at room temperature and then evaporated to dryness in vacuo, and the residue is extracted twice at 50° using 30 ml of acetonitrile and 30 ml of ethyl acetate each time. The residue is chromatographed on 60 g of silica gel with methylene chloride/methanol (95:5). The main fraction contains the desired compound having $R_f$=0.35 (chloroform:methanol=9:1).

In order to remove small amounts of Ca ions (0.36%) that are eluted from the silica gel during the chromatography, conversion into a different salt is effected using the sodium salt of ethylenediaminetetraacetic acid (EDTA) (from EDTA and 2N sodium hydroxide solution up to pH=7). 1.1 g of the salt mixture obtained above is dissolved at 30° in a mixture of 45 ml of dimethoxyethane and 5 ml of twice-distilled water; 60 ml of 0.2 molar EDTA/sodium salt solution of pH=7 are added, yielding a clear solution which is concentrated to a volume of 20 ml in vacuo yielding a suspension which is filtered with twice-distilled water over an ultrafilter in an Amicon agitator cell (exclusion limit 10 000 Daltons; Amicon PM 10) until the filtrate is EDTA-negative. The substance remains on the filter in the form of a gel and is precipitated by the addition of 100 ml of acetonitrile and dried in vacuo at 50°, yielding the sodium salt of N-(N-palmitoyl-S-[2(R),3-dilauroyloxy-propyl]-(R)-cysteinyl)-taurine; m.p. from 270° (decomp.); $[\alpha]_D^{20} = -10.3° \pm 2°$ (c=0.485; dimethyl sulfoxide), $[\alpha]_D^{20} = -6.0° \pm 1.9°$ (c=0.515; chloroform).

EXAMPLE 2

Analogously to Example 1, starting from N,N'-di(2-sodium-sulfonatoethyl)-L-glutamic acid diamide and N-palmitoyl-S-[2(R),3-dilauroyloxy-propyl]-(R)-cysteine there is obtained palmitoyl-Cys[2(R),3-dilauroyloxy-propyl]-Glu(NH—CH$_2$—CH$_2$—SO$_3^\ominus$Na$^\oplus$)—NH—CH$_2$—CH$_2$—SO$_3^\ominus$Na$^\oplus$; m.p. >250°, decomp. from 290°R$_f$=0.42 (chloroform:methanol:water=70:30:3), $[\alpha]_D^{20} = +1.2° \pm 1°$ (c=0.985; dimethyl sulfoxide).

The starting material is obtained in the following manner:

Step 2.1: 3.44 g of taurine dissolved in 13.74 ml of 2N sodium hydroxide solution are added to 8 g of N-benzyloxycarbonyl-L-glutamic acid di(2,4,5-trichlorophenyl) ester dissolved in 60 ml of dimethylacetamide. The mixture is stirred at room temperature for 15 hours. The pH value is then adjusted to 6 and the mixture is concentrated by evaporation in vacuo. The residue is taken up in twice-distilled water, trichlorophenol is removed by filtration with suction and washed with water. Concentration of the aqueous phase by evaporation yields a colourless resin which is extracted twice with 30 ml of diethyl ether at 40°, twice with 30 ml of acetone at 50° and twice with 30 ml of ethanol at 60°. The mixture is filtered with suction and the residue is extracted twice with 50 ml of methanol. Concentration of the methanol phase by evaporation yields the crude compound which is dissolved in 20 ml of twice-distilled water and precipitated with 120 ml of acetone, yielding benzyloxycarbonyl-Glu(NH—CH$_2$—CH$_2$—SO$_3^\ominus$Na$^\oplus$)—NH—CH$_2$—CH$_2$—SO$_3^\ominus$Na$^\oplus$;R$_f$=0.41 (chloroform:methanol:water=60:40:5), m.p. 229°-232° (decomp.).

Step 2.2: Starting from benzyloxycarbonyl-Glu(NH—CH$_2$—CH$_2$—SO$_3^\ominus$Na$^\oplus$)—NH—CH$_2$—CH$_2$—SO$_3^\ominus$Na$^\oplus$ there is obtained, by catalytic hydrogenation with palladium/carbon (10% Pd) in water and freeze-drying, N,N'-di-(2-sodium-sulfonatoethyl)-L-glutamic acid diamide in the form of an amorphous powder; R$_f$=0.39 (water; determined on thin-layer plates coated with silica gel UP-C$_{12}$ [silica gel charged with dodecyl radicals] by Antec).

EXAMPLE 3

1 g (1.25 mmol) of N-palmitoyl-S-[2(R,S),3-dilauroyloxy-propyl]-(R)-cysteine and 203 mg (1.5 mmol) of N-hydroxybenzotriazole are dissolved in 10 ml of absolute dimethylacetamide and cooled to 0°; 309 mg (1.5 mmol) of N,N'-dicyclohexylcarbodiimide are added and the mixture is stirred at 0° for 3 hours. A solution of 295 mg (1.5 mmol) of L-alanyltaurine and 220 μl of tetramethylguanidine in 10 ml of absolute dimethylacetamide is added and the mixture is stirred for 18 hours at room temperature. The mixture is concentrated by evaporation in vacuo and the residue is extracted once with 30 ml of ethyl acetate and once with 30 ml of methylene chloride. The solution is freed of precipitate and concentrated by evaporation, yielding the crude product which is dissolved in methylene chloride, and the N-hydroxybenzotriazole is extracted three times with saturated sodium hydrogen carbonate solution. The organic phase is concentrated by evaporation and the residue is extracted three times using 10 ml of acetonitrile each time. The solutions are cooled to 10° and the precipitate is removed by filtration with suction. The material that is insoluble in acetonitrile at 10° is converted into the sodium salt using the sodium salt of 2-ethylcaproic acid. For this purpose, the crude product is dissolved in 10 ml of chloroform; 7 ml of a 1-molar solution of the sodium salt of 2-ethylcaproic acid in methanol is added and the mixture is evaporated to dryness; the residue is extracted three times using 8 ml of ethyl acetate each time and the residue is chromatographed on 30 g of silica gel extracted with 6N hydrochloric acid (Merck). Elution is carried out first with methylene chloride, then with methylene chloride/acetone (1:1) and subsequently with methylene chloride/methanol/water (9:1:0.1). The substance is eluted with the latter two solvent mixtures. Palmitoyl-(R,S)-Cys[2(R,S),3-dilauroyloxy-propyl]-Ala—NH—CH$_2$—CH$_2$—SO$_3^\ominus$Na$^\oplus$ is obtained in the form of a colourless powder having a melting point of 228°-230°; $[\alpha]_D^{20} = -3.8° \pm 1.1°$ (c=0.877; chloroform:methanol=1:1); R$_f$=0.196 (chloroform:methanol=1:1). The L-alanyltaurine used as starting material is described in U.S. Pat. No. 4,666,886, Example 33.

Remarks: The chromatography on untreated silica gel results in the elution of small amounts of Ca ions by the substance. Analogously to Example 1, these can be exchanged by means of the sodium salt of ethylenediaminetetraacetic acid. The physical properties, such as optical rotation, melting point and R$_f$ value of the Na$^+$ and the mixed Na$^+$/Ca$^{++}$ salts, do not differ. In the coupling method described in Example racemisation takes place at the cysteine.

EXAMPLE 4

Analogously to Example 3, starting from palmitoyl-Cys[2(R,S),3-dilauroyloxy-propyl] and taurine there is obtained palmitoyl-(R,S)-Cys[2(R,S),3-dilauroyloxy-propyl]—NH—CH$_2$—CH$_2$—SO$_3^\ominus$Na$^\oplus$; R$_f$=0.29 (methylene chloride:ethanol=10:1), $[\alpha]_D^{20} = -0.6° \pm 1.2°$ (c=0.865; chloroform:methanol=1:1).

EXAMPLE 5

Tablets comprising 20 mg of active ingredient, for example one of the compounds of the formula I described in the preceding examples, are prepared in the customary manner in the following composition:

| Composition: | |
|---|---|
| Active ingredient | 20 mg |
| Wheat starch | 60 mg |
| Lactose | 50 mg |
| Colloidal silica | 5 mg |
| Talc | 9 mg |
| Magnesium stearate | 1 mg |
| | 145 mg |

Preparation: The active ingredient is mixed with some of the wheat starch, the lactose and colloidal silica, and the mixture is passed through a sieve. Some more wheat starch is made into a paste with 5 times the amount of water in a water bath, and the powder mixture is kneaded with this paste until a slightly kneadable composition has been formed.

The kneadable composition is pressed through a sieve of mesh size approx. 3 mm and dried, and the dry granules obtained are passed again through a sieve. The remainder of the wheat starch, the talc and the magnesium stearate are thereinafter admixed, and the mixture is compressed to give notched tablets of 145 mg weight.

What is claimed is:

1. A pharmaceutically acceptable salt of a aminosulfonic acid derivative of formula I

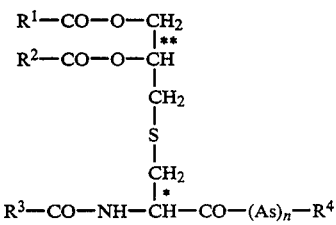

*(R)-configuration
**(R)- or (S)-configuration wherein
$R^1$, $R^2$ and $R^3$ are each independently of the others an aliphatic hydrocarbon radical having from 7 to 21 carbon atoms,
n is 0 or 1,
As is the amidically bonded residue of a (D)- or (L)-amino acid or of a (D)- or (L)-amino acid derivative from the group consisting of Gly, Ala, Ser, Thr, Asp, Asp($R^5$), Glu, Glu($R^5$), Gla, Gla($R^5$) and Gla($R^5$)$_2$, and
$R^4$ and $R^5$ are each independently of the other the amidically bonded radical of an unsubstituted or carboxy-substituted $\omega$-amino-$C_2$-$C_3$alkanesulfonic acid.

2. A pharmaceutically acceptable salt of a sulfonic acid derivative of formula I according to claim 1 wherein
$R^1$, $R^2$ and $R^3$ are each independently of the others $C_7$-$C_{21}$alkyl, $C_{17}$alkenyl or $C_{17}$alkynyl,
n is 0 or 1,
As is the amidically bonded residue of an amino acid or of an amino acid derivative from the group consisting of Ala and Glu($R^5$), and
$R^4$ and $R^5$ are each the amidically bonded radical of an $\omega$-amino-$C_2$-$C_3$alkanesulfonic acid.

3. A pharmaceutically acceptable salt of a sulfonic acid derivative of formula I according to claim 1 wherein
$R^1$ and $R^2$ are identical and are each straight-chain $C_{11}$-$C_{17}$alkyl,
$R^3$ is straight-chain $C_{11}$-$C_{17}$alkyl,
n is 0 or 1,
As is the amidically bonded residue of alanine or Glu(NH—$CH_2$—$CH_2$—$SO_3$H), and
$R^4$ is the amidically bonded radical of 2-aminoethanesulfonic acid.

4. A pharmaceutically acceptable salt of a sulfonic acid derivative of formula I according to claim 1 wherein in formula I $R^1$ is n-undecyl, $R^2$ is n-undecyl and $R^3$ is n-pentadecyl.

5. A pharmaceutically acceptable salt of a sulfonic acid derivative of formula I according to claim 2 wherein in formula I $R^1$ is n-undecyl, $R^2$ is n-undecyl and $R^3$ is n-pentadecyl.

6. A pharmaceutically acceptable salt of a sulfonic acid derivative of formula I according to claim 3 wherein in formula I $R^1$ is n-undecyl, $R^2$ is n-undecyl and $R^3$ is n-pentadecyl.

7. A pharmaceutically acceptable salt of N-(N-palmitoyl-S-[2(R),3-dilauroyloxy-propyl]-(R)-cysteinyl)-taurine according to claim 1.

8. A pharmaceutically acceptable salt of palmitoyl-Cys[2(R),3-dilauroyloxy-propyl]-Glu-(NH—$CH_2$—$CH_2$—$SO_3$H)—NH—$CH_2$—$CH_2$—$SO_3$H according to claim 1.

9. A pharmaceutical composition for stimulating the immune system of a warm-blooded animal comprising an immunostimulating effective amount of a pharmaceutically acceptable salt of a compound of formula I according to claim 1 together with a pharmaceutical carrier.

10. A method of stimulating the immune system of a warm-blooded animal comprising administering to a warm-blooded animal in need thereof an immunostimulating effective amount of a pharmaceutically acceptable salt of a compound of formula I according to claim 1.

* * * * *